United States Patent [19]
Gregory et al.

[11] Patent Number: 5,989,244
[45] Date of Patent: Nov. 23, 1999

[54] METHOD OF USE OF A SHEET OF ELASTIN OR ELASTIN-BASED MATERIAL

[76] Inventors: Kenton W. Gregory, 23200 Stafford Hill Dr., West Linn, Oreg. 97068; John M. Grunkemeier, 5655 12th Ave. NE., Seattle, Wash. 98105

[21] Appl. No.: 08/341,881

[22] Filed: Nov. 15, 1994

[51] Int. Cl.[6] .................................................. A61B 17/36
[52] U.S. Cl. ...................... 606/8; 128/898; 128/DIG. 8; 623/11
[58] Field of Search ................................. 623/11, 16, 66; 606/2, 3, 8, 10; 128/DIG. 8

[56] References Cited

U.S. PATENT DOCUMENTS

| | | |
|---|---|---|
| 4,132,746 | 1/1979 | Urry et al. . |
| 4,187,852 | 2/1980 | Urry et al. . |
| 4,500,700 | 2/1985 | Urry . |
| 4,589,882 | 5/1986 | Urry . |
| 4,693,718 | 9/1987 | Urry et al. . |
| 4,783,523 | 11/1988 | Urry et al. . |
| 4,801,299 | 1/1989 | Brendel et al. . |
| 4,870,055 | 9/1989 | Urry et al. . |
| 4,976,734 | 12/1990 | Urry et al. . |
| 5,064,430 | 11/1991 | Urry . |
| 5,209,776 | 5/1993 | Bass et al. . |
| 5,223,420 | 6/1993 | Rabaud et al. . |
| 5,292,362 | 3/1994 | Bass et al. . |
| 5,336,256 | 8/1994 | Urry . |
| 5,336,616 | 8/1994 | Livesey et al. . |

FOREIGN PATENT DOCUMENTS

WO/91/04073   4/1991   WIPO .

OTHER PUBLICATIONS

Ooyama et al, "Substratum–Bound Elastin Peptide Inhibits Aortic Smooth Muscle Cell Migration in Vitro", Arteriosclerosis 7(6):593–598 (1987).

Long et al, "Elastin Repeat Peptides as Chemoattractants for Bovine Aortic Endothelial Cells", Journal of Cellular Physiology 140:512–518 (1989).

Aprahamian et al, "A new reconstituted connective tissue matrix: Preparation, biochemical, structural and mechanic studies", Hournal of Biomedical Materials Research 21:965–977 (1987).

Rabaud et al, "Soluble Fibrinogen Derivatives Generated by Thrombin: Affinity for Elastin", Thrombosis Research 43:205–211 (1986).

Martin et al, "Biochemical study of adduct synthesis between fibrin monomers and elastin", Biomaterials 9:519–524 (1988).

Lefebvre et al, "New artificial connective matrix–like structure made of elastin solubilized peptides and collagens: elaboration, biochemical and structural properties", Biomaterials 13(1):28–33 (1992).

Pool et al, "Production of High–Potency Concentrations of Antihemophilic Globulin in a Closed–Bag System", The New England Journal of Medicine 273(27):1443–1447 (1965).

Landsman et al, "Light–absorbing properties, stability, and spectral stabilization of indocyanine green", Journal of Applied Physiology 40(4):575–583 (1976).

Crissman, Robert S., "Comparison of Two Digestive Techniques for Preparation of Vascular Elastic Networks for SEM Observation", Journal of Electron Microscopy Technique 6:335–348 (1987).

Guisti et al, "Bioartificial Polymeric Materials: A New Method to Design Biomaterials by using both Biological and Synthetic Polymers", TRIP 1(9):261–267 (1993).

*Primary Examiner*—Robert A. H. Clarke
*Attorney, Agent, or Firm*—Marger, Johnson, McCollom & Stolowitz, P.C.

[57] ABSTRACT

The present invention relates to an elastin-based biomaterial and to a method of using same to effect tissue repair or replacement. The invention further relates to a method of securing the biomaterial to existing tissue.

33 Claims, 6 Drawing Sheets

METHOD OF USE OF A SHEET OF ELASTIN OR ELASTIN-BASED MATERIAL

TECHNICAL FIELD

The present invention relates to elastin-based biomaterials and to methods of using same in tissue repair and replacement. The invention further relates to methods of securing the biomaterials to existing tissue.

BACKGROUND OF THE INVENTION

Elastin is an extracellular matrix protein that is ubiquitous in mammals. Elastin is found, for example, in skin, blood vessels, and tissues of the lung where it imparts strength, elasticity and flexibility. In addition, elastin, which is prevalent in the internal elastic lamina (IEL) and external elastic lamina (EEL) of the normal artery, may inhibit the migration of smooth muscle cells into the intima. Elastin in the form of solubilized peptides has been shown to inhibit the migration of smooth muscle cells in response to platelet-derived factors (Ooyama et al, Arteriosclerosis 7:593 (1987)). Elastin repeat hexapeptides attract bovine aortic endothelial cells (Long et al, J. Cell. Physiol. 140:512 (1989)) and elastin nonapeptides have been shown to attract fibroblasts (U.S. Pat. No. 4,976,734). The present invention takes advantage of these physical and biochemical properties of elastin.

Thirty to forty percent of atherosclerotic stenoses that are opened with balloon angioplasty restenose as a result of ingrowth of medial cells. Smooth muscle ingrowth into the intima appears to be more prevalent in sections of the artery where the IEL of the artery is ripped, torn, or missing, as in severe dilitation injury from balloon angioplasty, vessel anastamoses, or other vessel trauma that results in tearing or removal of the elastic lamina. While repair of the arterial wall occurs following injury, the elastin structures IEL and EEL do not reorganize. Since these components play major structural and regulatory roles, their destruction is accompanied by muscle cell migration.

There are also diseases that are associated with weakness in the vessel wall that result in aneurysms that can ultimately rupture, as well as other events that are, at least in part, related to abnormalities of elastin.

Prosthetic devices, such as vascular stents, have been used with some success to overcome the problems of restenosis or re-narrowing of the vessel wall resulting from ingrowth of muscle cells following injury. However, their use is often associated with thrombosis. In addition, prosthetic devices can exacerbate underlying atherosclerosis. Nonetheless, prostheses are often used.

Until relatively recently, the primary methods available for securing a prosthetic material to tissue. (or tissue to tissue) involved the use of sutures or staples. Fibrin glue, a fibrin polymer polymerized with thrombin, has also been used (primarily in Europe) as a tissue sealant and hemostatic agent.

Laser energy has been shown to be effective in tissue welding arterial incisions, which is thought to occur through thermal melting of fibrin, collagen and other proteins. The use of photosensitizing dyes enhances the selective delivery of the laser energy to the target site and permits the use of lower power laser systems, both of which factors reduce the extent of undesirable thermal trauma.

The present invention combines the advantages of elastin-based products with the advantages of laser welding techniques, and provides a unique method of tissue repair and replacement. The invention makes possible tissue prostheses (particularly, vascular prostheses) that are essentially free of problems associated with prostheses known in the art.

OBJECTS AND SUMMARY OF THE INVENTION

It is a general object of the invention to provide a method of effecting tissue repair or replacement.

It is a specific object of the invention to provide an elastin-based biomaterial suitable for use as a stent, for example, a vascular stent, or as conduit replacement, for example, as an artery, vein or a ureter replacement. The biomaterial can also be used as a stent or conduit covering or lining.

It is a further object of the invention to provide an elastin-based graft suitable for use in repairing a lumen wall.

It is another object of the invention to provide an elastin-based material suitable for use in tissue replacement or repair, for example, in interior bladder replacement or repair, in intestine, esophagus or colon repair or replacement, or skin repair or replacement.

It is also an object of the invention to provide a method of securing an elastin-based biomaterial to an existing tissue without the use of sutures or staples.

The present invention relates to a method of repairing, replacing or supporting a section of a body tissue. The method comprises positioning an elastin-based biomaterial at the site of the section and bonding the biomaterial to the site or to the tissue surrounding the site. The bonding is effected by contacting the biomaterial and the site, or tissue surrounding the site, at the point at which said bonding is to be effected, with an energy absorbing agent. The agent is then exposed to an amount of energy absorbable by the agent sufficient to bond the biomaterial to the site or to the tissue surrounding the site.

Further objects and advantages of the invention will be clear from the description that follows.

DETAILED DESCRIPTION OF THE INVENTION

The present invention relates to elastin-based biomaterials and to methods welding of such biomaterials to tissue using laser energy. Elastin-based biomaterials suitable for use in the present invention can be prepared, for example, from elastin (eg from bovine nuchal ligament), fibrinogen and thrombin as described by Rabaud et al (U.S. Pat. No. 5,223,420). (See also Aprahamian et al, J. Biomed. Mat. Res. 21:965 (1987); Rabaud et al, Thromb. Res. 43:205 (1986); Martin, Biomaterials 9:519 (1988).) Such biomaterials can have associated thrombogenic properties that can be advantageous in certain types of tissue repair. Elastin-based biomaterials suitable for use in the invention can also be prepared from elastin and type III collagen, also as described by Rabaud and co-workers (Lefebvre et al, Biomaterials 13(1):28–33 (1992)). Such preparations are not thrombogenic and thus can be used for vascular stents, etc. A further type of elastin-based biomaterial suitable for use in the present invention is prepared as described by Urry et al (see, for example, U.S. Pat. Nos. 4,132,746 and 4,500,700). (See also U.S. Pat. Nos. 4,187,852, 4,589,882, 4,693,718, 4,783,523, 4,870,055, 5,064,430, 5,336,256). Elastin matrices resulting from digestion of elastin-containing tissues (eg arteries) can also be used. Digestion results in the removal of cells, proteins and fats but maintenance of the intact elastin matrix. The biomaterial used will depend on the particular application.

Elastin-based biomaterial of the invention prepared from soluble elastin (see Rabaud et al above) can be molded so as to render it a suitable size and shape for any specific purpose. Molded biomaterial can be prepared as follows. Elastin (eg soluble elastin (MW 12–32,000 daltons) is washed and swollen in buffer. Fibrinogen or cryoglobulins (prepared, for example, according to Pool et al, New Engl. J. Med. 273 (1965)) are added to the swollen elastin, followed by thiourea, with or without a protease inhibitor (such as aprotinin), and collagen. Thrombin is added with stirring and the resulting mixture is immediately poured into an appropriate mold. The mold is then incubated (for example, at 37° C.) while polymerization of the fibrin/elastin material is allowed to proceed, advantageously, for from between 15 minutes to 1 hour, 30 minutes being preferred. The reaction can be carried out at temperatures less than 37° C., but the reaction proceeds more rapidly at 37° C. Heating the reaction to over 40° C., however, can result in denaturation of the thrombin. Cooling of the mixture while stirring allows more time for mixing to occur. For polymerization to occur, it is important to have calcium and magnesium in the buffer and to use undenatured thrombin.

Following polymerization in the mold, the resulting biomaterial can be further cross-linked using gamma radiation or an agent such as glutaraldehye (a solution of glutaraldehye, formic acid and picric acid being preferred). When radiation is used, the samples are, advantageously, subjected to gamma-irradiation from a Cobalt-60 source. The amount of irradiation can range, for example, from 10 to 100 MRAD, with 25 MRAD being preferred. It has been shown that the amount of gamma-irradiation can affect the strength of the material (Aprahamian, J. Biomed. Mat. Res. 21:965 (1987)).

Sheets of biomaterial can be prepared that are of a controlled thicknesses by using appropriate molds. Sheets of the biomaterial can be made in thicknesses ranging, for example, from 200 microns to 5 mm. Sheets are generally made as thin as possible to allow for penetration of laser energy while maintaining sufficient strength. By way of example, a sheet suitable for use as an intestinal patch can range in thickness from 200 microns to 5 mm, with about 2 mm being preferred. A patch requiring greater strength, such a patch for use in the bladder, is typically thicker. Arterial stents or patches can be thinner (eg 100 $\mu$m–1000 $\mu$m).

Biomaterial prepared from soluble elastin or insoluble elastin fragments can also be molded into tubular segments for example, by injecting the material into tubular molds. Crosslinkage of the elastin solution present between the inner and outer tubes can be effected prior to withdrawal of biomaterial from the mold or after the tubes are removed. Tubular segments of different inner and outer diameters, as well as of different lengths, can be prepared using this approach by varying the diameters of the inner and outer tubes. A mold of this type can be made in virtually any size with the inner and outer tubes varying in diameter. A small tube can be used for a coronary arterial stent. A large tube of 1–5 inches in diamater can be made and used as an annularly welded patch for anastomosis of the small intestine or colon. Various molding techniques and molding materials can be used; the foregoing is merely an example.

As indicated above, biomaterial suitable for use in the present invention can be prepared from digests of tissue containing an elastin matrix. Tissues suitable for use as a starting material include arteries (e.g. coronary or femoral arteries, for example, from swine), umbilical cords, intestines, ureters, etc. Preferably, the matrix material is derived from the species of animal in which the implantation is being performed so that biocompatibility is increased. Any method of removing (digesting away) cellular material, proteins and fats from the native matrix while leaving the extracellular elastin matrix intact can be used. These methods can involve a combination of acidic, basic, detergent, enzymatic, thermal or erosive means, as well as the use of organic solvents. This may include incubation in solutions of sodium hydroxide, formic acid, trypsin, guanidine, ethanol, diethylether, acetone, t-butanol, and sonication. Typically, the digestion proceeds more quickly at higher temperatures. The optimal temperature and time of incubation depend on the starting material and digestive agent used, and can be readily determined.

One skilled in the art will appreciate that while tubular segments result from digestion of tubular starting materials, those segments can be opened and shaped to yield sheets suitable for use as tissue grafts. Alternatively, such segments can be opened and then reconstructed as tubular segments having a diameter different than the starting tissue. Preferably, however, when tubular products are sought, the starting material is selected so as to yield a tubular segment after digestion having the appropriate diameter so that subsequent manipulations (other than adjustment of length) can be avoided.

The biomaterial of the invention, whether prepared from elastin powder or from tissue digests, is normally secured to existing tissue. Various techniques for effecting that attachment can be used, including art-recognized techniques. However, it is preferred that the biomaterial be secured using a tissue welding energy source and an agent that absorbs energy emitted by that source. Advantageously, the energy source is an electromagnetic energy source, such as a laser, and the absorbing agent is a dye having an absorption peak at a wavelength corresponding to that of the laser. The elastin biomaterial and the tissue to be welded have much less absorption of light at this wavelength and the effect therefore is confined to a zone around the dye layer. A preferred energy source is a laser diode having a dominant wavelength at about 808 nm and a preferred dye is indocyanine green (ICG), maximum absorbance 795–805 nm (see WO 91/04073). Other laser/dye combinations can also be used. It is preferred that the dye be applied to that portion of the biomaterial that is to be contacted with and secured to the existing tissue. The dye can also be applied to the surface of the structure to which the elastin biomaterial is to be welded or secured. The dye can be applied directly to the biomaterial or the surface of the biomaterial can first be treated or coated (eg primed) with a composition that controls absorption of the dye into the biomaterial so that the dye is kept as a discrete layer or coating. Alternatively, the dye can be bound to the elastin biomaterial so that it is secured to the surface and prevented from leeching into the material. The dye can be applied in the form of a solution or the dye can be dissolved in or suspended in a medium which then can be applied as a thin sheet or film, preferably, of uniform thickness and dye concentration.

Tissue welding techniques employing a soldering agent can be used. Such techniques are known (WO 91/04073). Any proteinaceous material that thermally denatures upon heating can be used as the soldering agent (for example, any serum protein such as albumin, fibronectin, Von Willebrand factor, vitronectin, or any mixture of proteins or peptides). Solders comprising thrombin polymerized fibrinogen are preferred, except where such materials would cause undesirable thrombosis or coagulation such as within vascular lumens. Solders are selected for their ability to impart greater adhesive strength between the biomaterial and the tissue. The solder should be non-toxic and generally biocompatible.

Figure 1:
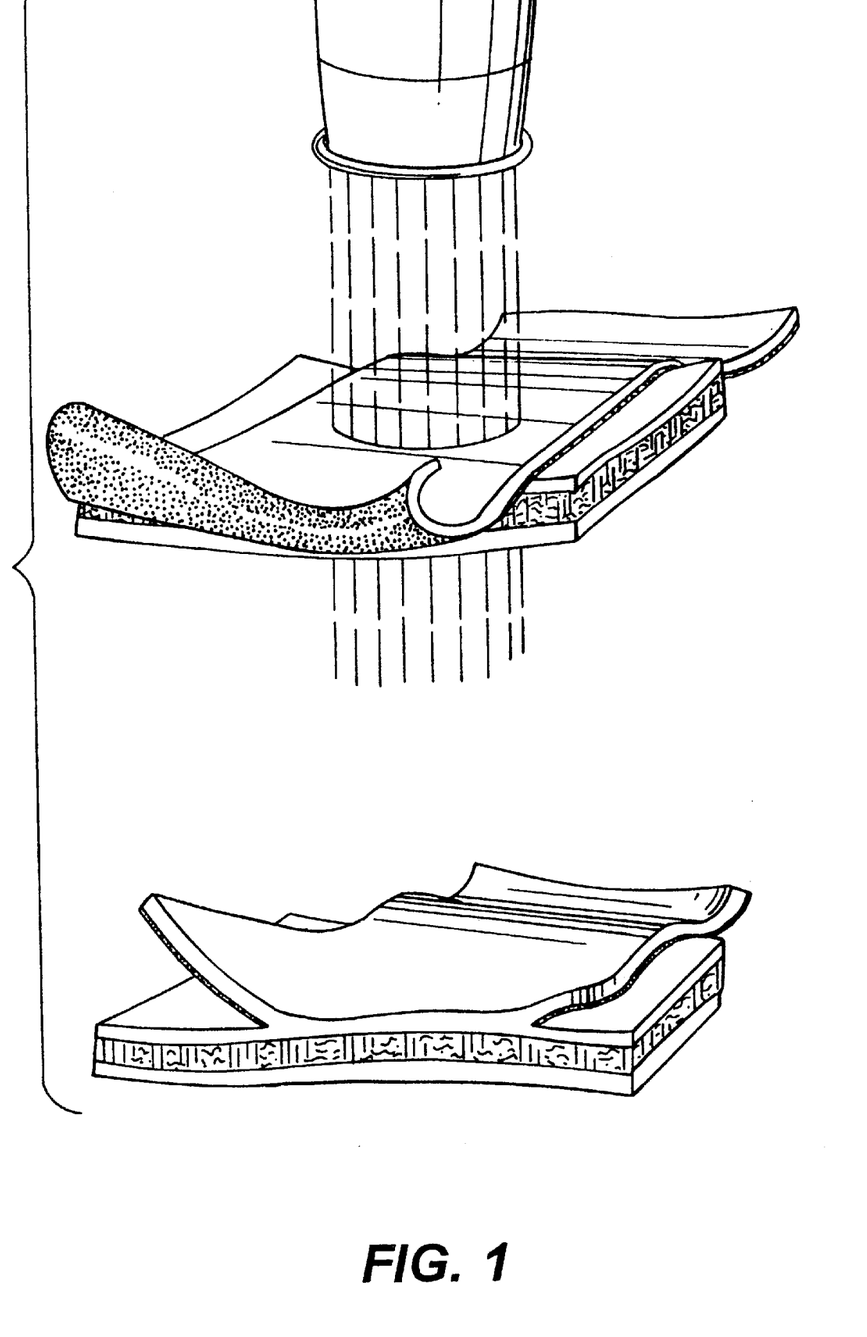
FIG. 1. Application of laser energy to biomaterial and exposed native tissue.

In accordance with the present invention, the laser energy can be directed to the target site (eg, the dye) directly from the laser by exposure of the tissue (eg, during a surgical procedures). In some cases, ie endovascular catheter-based treatments where open surgical exposure does not occur, the laser energy is directed to the bonding site via optical fibers. When ICG is used as the dye, targeting media wavelengths of around 800 nm can be used. Such wavelengths are not well absorbed by many tissues, particularly vascular tissues, therefore, there will be a negligible effect on these tissues and thermal effects will be confined to the dye layer. The biomaterial of the invention similarly has little optical absorbance in this waveband, as compared to the energy absorbing dye. Thus, the laser energy can pass through either the biomaterial or the native tissue and be absorbed by the dye layer as shown in FIG. 1. Once the surgeon has exposed the surface or vessel where the biomaterial reinforcement or replacement is to be effected, the dye-containing surface of the biomaterial is placed in contact with the native tissue at the site and laser energy delivered by directing the laser beam to the desired location. The absorbance of the dye (eg ICG) layer is ideally previously or concurrently determined so that the optimal amount of light for optimal bonding can be delivered. Pressure can be used to ensure adequate approximation of the tissue and biomaterial. With a diode laser source, the diode laser itself, or a condenser or optical fiber based optical delivery system, can be placed against the material to ensure uniform light delivery.

Figure 2:
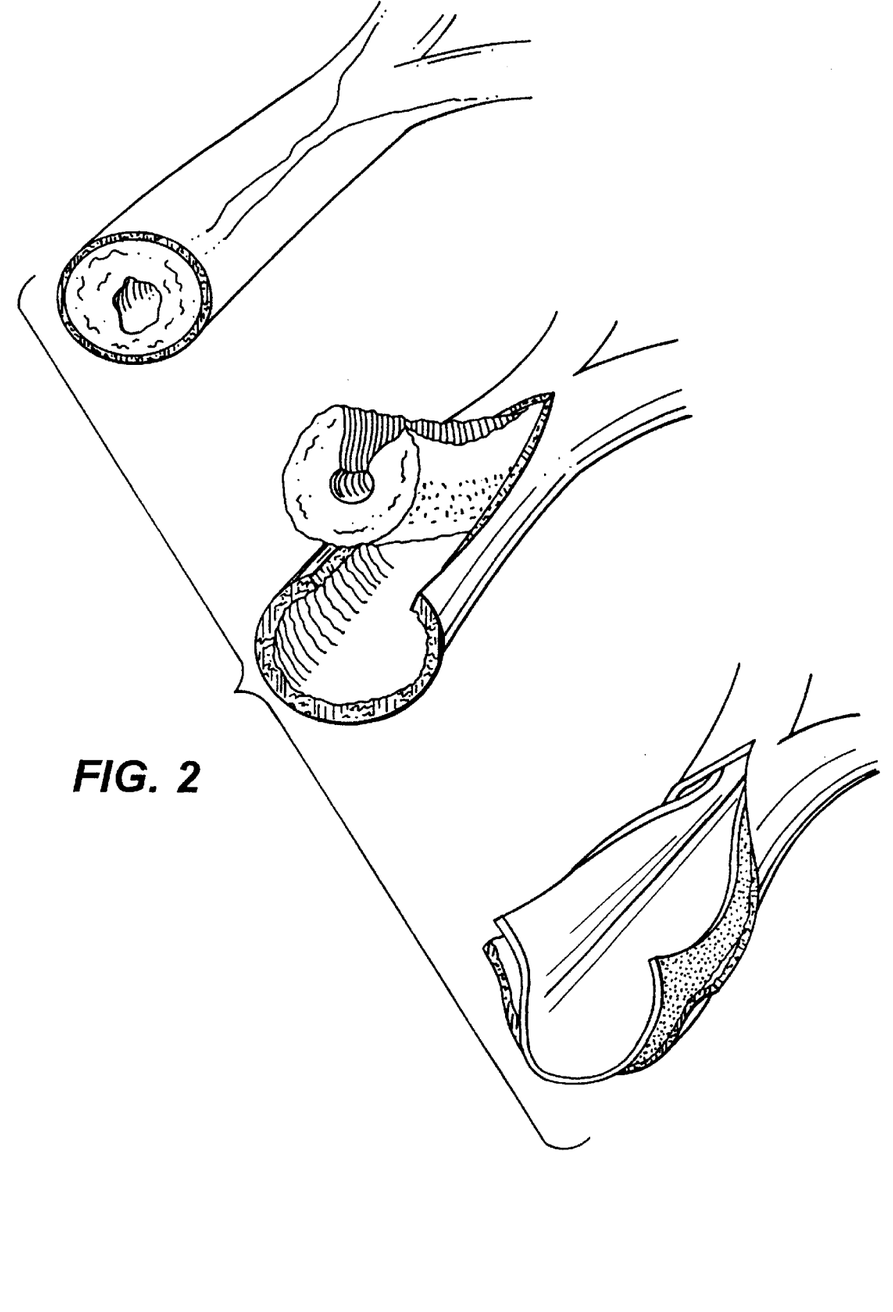
FIG. 2. Placement of elastin biomaterial into artery.
Figure 4:
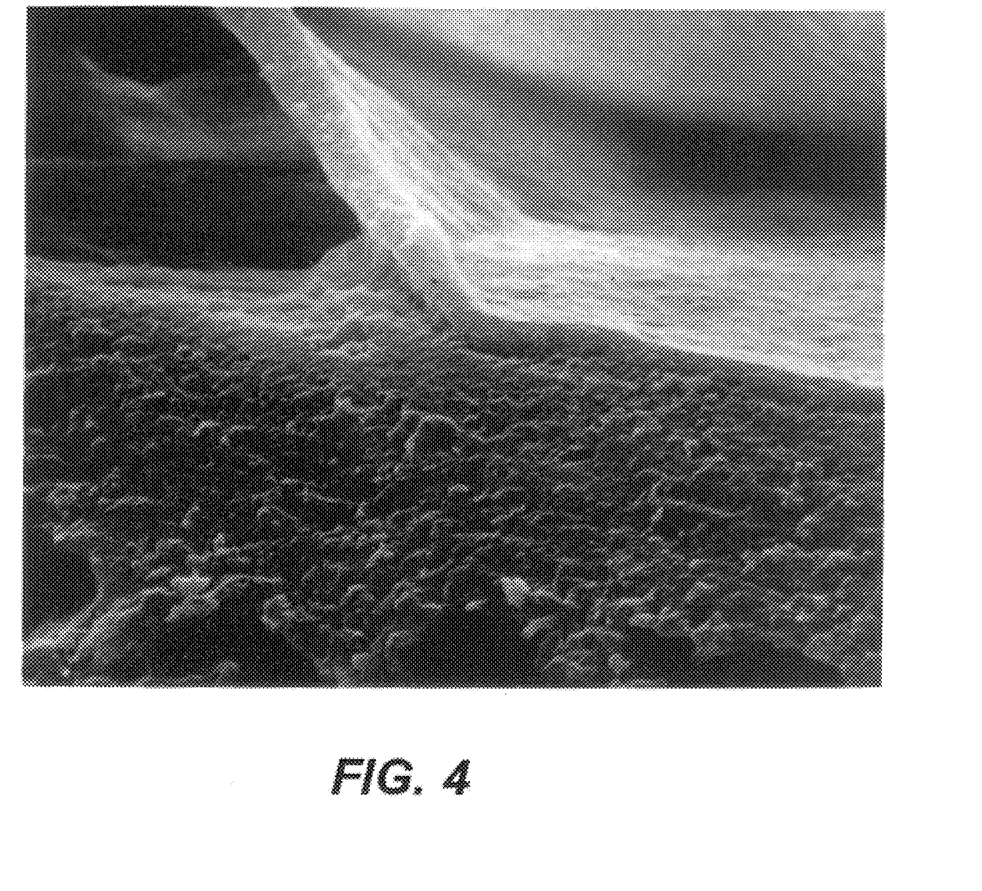
FIG. 4. Scanning electron micrograph of elastin-based biomaterial (prepared according to Rabaud et al using elastin, fibrinogen and thrombin) fused to procine aorta using continuous wave diode laser.

In cases where a new elastin lining or new-internal elastic lamina is required, for example, following an open surgical endarterectomy, once the artery has been surgically cleared of the atheroma or other lesion, the biomaterial is then put in place, dye side down (see FIG. 2). The biomaterial can be deployed as a flat patch or as a tubular segment. A tubular segment can be hollow or filled with a material that supports the lumen during placement and that is melted with low grade heat or dissolved or removed with a variety of means. When necessary, a small number of surgical sutures (eg stay sutures) can be used to appose the edges of the vessel together or to sew the vessel. Once the biomaterial is in place, the laser energy is directed through the vessel wall or through the biomaterial to the absorbing dye, the appropriate laser energy having been previously determined based upon the measured absorbance in the biomaterial. Alternatively, the dye can be appled at the time of the surgery to the biomaterial or the vessel wall or both and then laser energy delivered. In this embodiment, absorbance can be determined at the time of deployment or empirically delivered or with a feedback device that assesses the adequacy of the bonding or thermal effect. (FIG. 4 is a SEM of elastin-based biomaterial fused to porcine aorta.)

Figure 3:
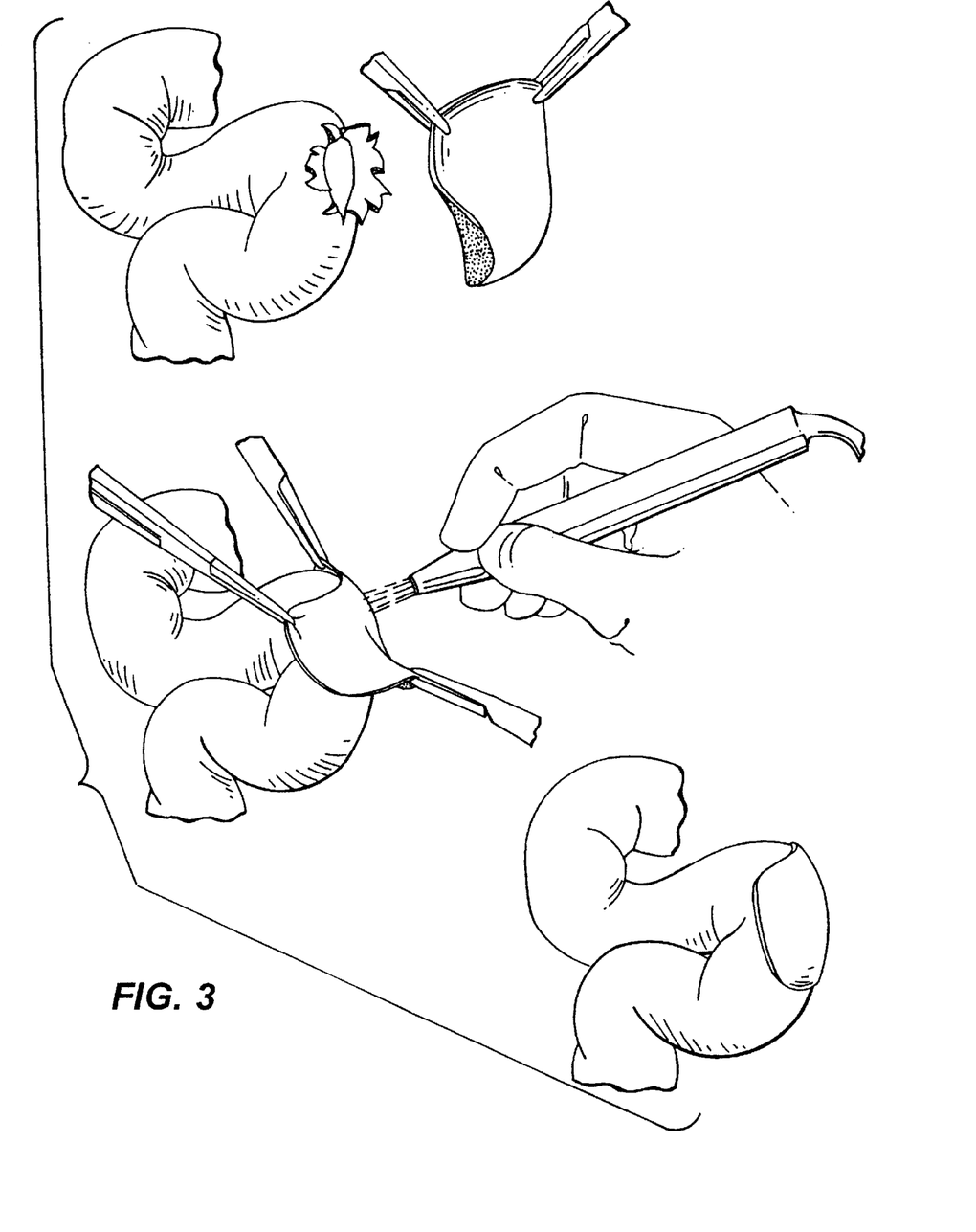
FIG. 3. Use of biomaterial as intestinal patch.

In addition to the above, the biomaterial of the invention can be used as a patch material for use in intestinal or colon repairs which frequently do not heal well with current techniques, particularly when the patient has nutritional or other problems or when the patient is in shock, such as in the case of multiple gunshot wounds or other abdominal injuries (see FIG. 3). The use of such a patch can, for example, seal off intestinal contents and thereby reduce the likelihood of peritonitis. In addition, a patch can be used on a solid organ, such as the liver, when lacerations have occurred. Similarly, the biomaterial of the invention can be used to repair or replace portions of the urinary system i.e., from the calyces of the kidney on down to the urethra. The patch can also be used to seal a defect in a cardiac chamber, such as an atrial septal defect, as well as bronchial or rectal fistulas. The biomaterial can also be used as a cerebrovascular patch for an aneurysm. The biomaterial can be sealed in place with targeted laser fusion. For applications where direct exposure is not possible or not desirable, a variety of catheter or endoscopic systems can be employed to direct the laser energy to the target site.

The elastin-based biomaterials to which the invention relates can be used in a variety of other clinical and surgical settings to effect tissue repair and replacement. The biomaterial can be used as a vascular stent, as described above, or as a vascular graft. For delivery of biomaterial in the form of an intravascular stent, the biomaterial can be pre-mounted upon a deflated balloon catheter. The balloon catheter can be maneuvered into the desired arterial or venous location using standard techniques. The balloon can then be inflated, compressing the stent (biomaterial) against the vessel wall and then laser light delivered through the balloon to seal the stent in place (the dye can be present on the outside of the biomaterial). The balloon can then be deflated and removed leaving the stent in place. A protective sleeve (eg of plastic) can be used to protect the stent during its passage to the vessel and then withdrawn once the stent is in the desired location.

The biomaterial of the invention can also be used as a biocompatible covering for a metal or synthetic scaffold or stent. In such cases, simple mechanical deployment can be used without the necessity for laser bonding. Laser bonding can be employed, however, depending upon specific demands, eg, where inadequate mechanical bonding occurs, such as in stent deployment for abdominal aortic aneurysms.

An alternative catheter-based vascular stent deployment strategy employs a temporary mechanical stent with or without a balloon delivery device.

A further catheter-based vascular stent deployment strategy employs a heat deformable metal (such as nitinol or other similar type metal) scaffold or stent or coating that is incorporated into the catheter tubing beneath the stent biomaterial. The stent is maneuvered into the desired location whereupon the deformable metal of the stent is activated such that it apposes the stent against the vessel wall. Laser light is then delivered via an optical fiber based system, also incorporated into the catheter assembly.

The elastin-based biomaterial can also be used to replace portions of diseased or damaged vascular or nonvascular tissue such as esophagus, paracardium, lung plura, etc. The biomaterial can also be used as a skin layer replacement, for example, in burn or wound treatments. As such, the biomaterial serves as a permanent dressing that acts as a scaffolding for epithelial cell regrowth. The biomaterial can include antibiotics, coagulants or other drugs desirable for various treatments that provide high local concentrations with minimal systemic drug levels. The elastin biomaterial can be deployed with a dye on the tissue side and then fused with the appropriate wavelength and laser energy.

In addition to repair of tubular body structures, the biomaterial of the present invention can also be used in organ reconstruction. For example, the biomaterial can be molded or otherwise shaped as a pouch suitable for use in bladder reconstruction. The biomaterial of the invention can also be molded or otherwise shaped so as to be suitable for esophageal replacement. Again, metal or synthetic mesh could also be associated with the implant if extra wall support is needed so as to control passage of food from the pharynx to the stomach. This could be used for stenosis of the esophagus, repair from acid reflux for erosive esophagitis or, more preferably, for refurbishing damaged esophageal segments during or following surgery or chemotherapy for esophageal carcinoma.

For certain applications, it may be desirable to use the biomaterial of the invention in combination with a supporting material having strong mechanical properties. For those applications, the biomaterial can be coated on the supporting material (see foregoing stent description), for example, using the molding techniques described herein. Suitable supporting materials include polymers, such as woven polyethylene terepthalate (Dacron), teflon, polyolefin copolymer, polyurethane polyvinyl alcohol or other polymer. In addition, a polymer that is a hybrid between a natural polymer, such as fibrin and elastin, and a non-natural polymer such as a polyurethane, polyacrylic acid or polyvinyl alcohol can be used (see Giusti et al, Trends in Polymer Science 1:261 (1993)). Such a hybrid material has the advantageous mechanical properties of the polymer and the desired biocompatibility of the elastin based material. Examples of other prostheses that can be made from synthetics (or metals) coated with the elastin biomaterial or from the biomaterial/synthetic hybrids include cardiac valve rings and esophageal stents.

The elastin-based prostheses of the invention can be prepared so as to include drugs that can be delivered, via the prostheses, to particular body sites. For example, vascular stents can be produced so as to include drugs that prevent coagulation, such as heparin, or antiplatelet drugs such as hirudin, drugs to prevent smooth muscle ingrowth or drugs to stimulate endothelial regrowth. Vasodilators can also be included. Prostheses formed from the elastin based biomaterial can also be coated with viable cells, preferable, cells from the recipient of the prosthetic device. Endothelial cells, preferably autologous (eg harvested during liposuction), can be seeded onto the elastin bioprosthesis prior to implantation (eg for vascular stent indications). Alternatively, the elastin biomaterial can be used as a skin replacement or repair media where cultured skin cells can be placed on the biomaterial prior to implantation. Skin cells can thus be used to coat elastin biomaterial.

Certain aspects of the invention are described in greater detail in the non-limiting Examples that follow.

EXAMPLE 1

Preparation of Sheets of Elastin-Based Biomaterial from Soluble Peptides

Materials used for biomaterial production:

Phosphate buffer: The phosphate buffer used contained 1 mM sodium phosphate, 150 mM sodium chloride, 2 mM calcium chloride, 1 mM magnesium chloride, pH 7.4.

Soluble elastin peptides: Bovine ligamentum nuchae elastin powder was obtained from Sigma, St. Louis, Mo. The following procedure was used to obtain the soluble elastin peptides: 2.7 g elastin powder was suspended in 35 ml of a 1 M KOH solution in 80% ethanol. The suspension was stirred at 50° C. for 2.5 hr. Next, 10 ml deionized water was added and the solution neutralized with concentrated 12 M HCl to pH 7.4. The solution was cooled at 4° C. for 12 hrs. The clear solution was decanted from the salt crystals, and the supernatant centrifuged for 15 mins at 2000 rpm. The solution was then dialyzed against three changes of tap water at two hour intervals and one 15 hr interval using a 10,000 MW cutoff dialysis tubing. The dialysis was continued with six changes of deionized water at two hour intervals and one for 15 hrs. The resulting dialyzate was lyophilized and stored at −20° C. The yield was 40%.

Cryoglobulin preparation: A modification of the method of Pool and Shannon was used to produce the cryoglobulins (New Engl. J. Med. 273 (1965)). Cryoglobulins are principally fibrinogen (40 mg/ml) and fibronectin (10 mg/ml) (concentrations of fibrinogen and fibironectin will vary). Briefly, blood was collected from swine in a standard 500 ml blood collection bag containing adenine, citrate and dextrose anticoagulant. The blood was transferred to twelve 50 ml plastic centrifuge tubes and centrifuged for 15 mins at 1500 rpm. The plasma was decanted from the erythrocyte layer and frozen at −70° C. for 12 hrs. The plasma was then thawed at 4° C. The cryoglobulins were collected by centrifugation of the plasma at 4° C. for 15 mins at 1500 rpm. The supernatant was decanted and the cryoglobulins collected by removing the precipitate with a pasteur pipette. Each tube was also rinsed with 3 ml of a sodium citrate solution containing 0.9% NaCl, and 0.66% sodium citrate. The cryoglobulins were pooled, frozen at −70° C., lyophilized and stored at −20° C. until use.

Thiourea: Reagent grade thiourea was obtained from Sigma, St. Louis, Mo. A 0.5 mg/ml solution was used.

Type I collagen: Acid soluble type I collagen was obtained from Sigma. It was prepared from rat tail tendon by a modification of the method of Bornstein. Two mg of collagen was heated in 0.6 ml phosphate buffer to 60° C. for 10 minutes until the collagen dissolved. It was then cooled to 37° C. and used.

Thrombin: Thrombin from bovine plasma was obtained from Sigma in lyophilized from. When reconstituted with 1 ml water, the solution contained 106 NIH units per ml.

Aprotinin: Aprotinin from bovine lung was obtained from Sigma. It contained 15–30 trypsin inhibitory units (TIU) per ml.

Preparation:

Six molds were made by gluing a 620 μm quartz fiber to one side of a glass plate ˜40 mm×25 mm and attaching a second glass plate to the first using a rubber band. Each mold so constructed held about 0.5 ml.

The biomaterial was prepared by successively adding and mixing the following:

200 mg soluble kappa-elastin or kappa-elastin powder in 2 ml phosphate buffer (PB) (1 mM $PO_4$, 150 mM NaCl, 2 mM $Ca_2$, 1 mM $Mg_2$, pH 7.4) at 37° C.

160 mg cryoglobin in 1 ml PB (37° C.)

2 mg collagen in 0.6 ml PB (60°C.→37° C.)

200 μl thiourea (0.5 mg/ml)

200 μl aprotinin (5 Units)

A 0.6 ml aliquot of the above solution was loaded into a test tube and 50 μl thrombin solution was added (˜6 units). The resulting solution was immediately loaded into the mold. Certain of the resulting sheets were crosslinked with glutaraldehye for 2 mins.

Results:

The sheets prepared as described above were slightly yellowish and opaque. The glutaraldehye-fixed sheets were less stretchy and tore more easily than non-fixed sheets. Glutaraldehye fixed sheets were subjected to election microscopy. These sheets had a smooth cohesive surface appearance at 100× and 100×.

EXAMPLE 2

Tissue Welding of Sheets of Elastin-Based Biomaterial

Pre-welding procedure: A 1 mg/ml ICG solution was applied to fresh swine aorta that had been carefully trimmed of adventitia, washed in a sterile 0.9% NaCl solution, and cut into 1 cm2 squares. The 1 mg/ml ICG solution was applied to the lumenal side of the aorta for ~3 min and wiped off. (ICG was obtained from Sigma and contained 90% dye and 10% sodium iodide. Absorption coefficient measured at 780 nm with a $7.25 \times 10^{-6}$ M solution was found to be 175,000 $M^{-1}cm^{-1}$. The adsorption maximum shifts to 805 nm when ICG is bound to serum proteins (Landsman et al, J. Appl. Physiol. 40 (1976)).) A small amount of cryoglobulins, containing approximately 40 mg/ml fibrinogen and 10 mg/ml fibronectin doped with ICG, was also applied and the biomaterial placed on it. The two materials were placed between two glass slides. This was submerged in a 0.9% saline solution.

Welding procedure: Sheets of biomaterial made as described in Example 1 were equilibrated in phosphate buffer, pH 7.4, and welded to ICG stained porcine aorta using an aluminim gallium arsenide diode array laser. The maximum output was at 808±1.5 nm. The laser was coupled to a 1 μm quartz fiber with polyethylene cladding material. The laser energy was collimated with a focusing lens and coupled to the quartz fiber. The spot size at the distal end of the fiber could be varied from 1 mm to 4 mm by adjusting the distance between the focusing lens and the proximal end of the fiber. The laser operated continuously, CW, and the output measured at the distal end of the fiber was 1.5 W.

The quartz fiber was positioned directly above the glass slide, biomaterial, aorta. Before welding, the spot size of the laser was measured. Welding appeared to occur under saline at irradiances of $$\frac{0.85W}{cm^2}$$

but not at $$\frac{1.32W}{cm^2}.$$

Twenty seconds was sufficient time to weld and 40 seconds caused a brown color change and charring of the biomaterial.

EXAMPLE 3

Preparation of Elastin-Based Biomaterial from Artery Digest

Fresh 4 cm lengths of porcine carotid artery were dissected clean and washed in two changes of 0.9% saline overnight. Vessels were then placed in 0.5 M NaOH and sonicated for 120 minutes (a modified method of Crissman, R. 1987) (Crissman, Robert S. "Comparison of Two Digestive Techniques for Preparation of Vascular Elastic Networks for SEM Observation", Journal of Electron Microscopy Techniques 6:335–348 (1987)). Digested vessels were then washed in distilled water and autoclaved at 225° F. for 30 minutes. Digested vessels appear translucent, pearly white in color and collapsed when removed from water indicating the absence of collagen and other structurally supportive proteins.

Figure 6:
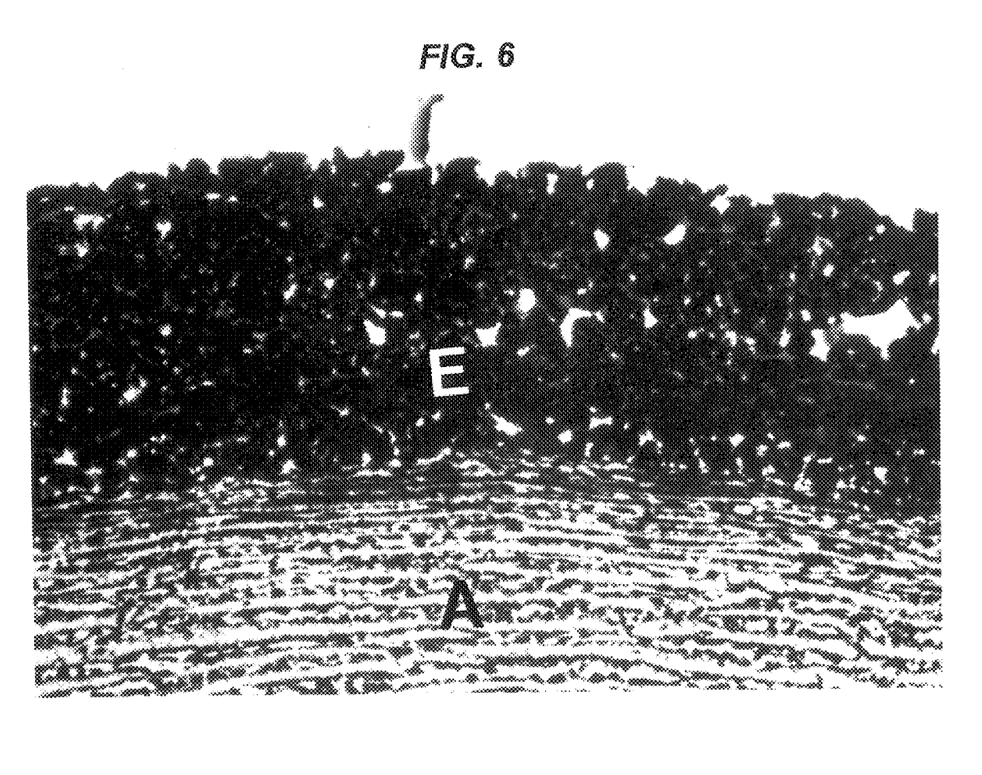
FIG. 6. Light microscopic photomicrograph of elastin-based biomaterial derived from arterial digest welded to porcine carotid artery. E=elastin biomaterial; A=aorta.

Welding of the artery digests to porcine aorta was accomplished through the following methods. Fresh porcine aorta was coated with 5 mg/ml ICG for 5 minutes. Eexcess ICG solution was blotted off. One x one cm sections of NaOH-sonicated digested carotid artery elastin segments were placed upon the freshly stained aortas. An array of pulsed aluminum gallium arsenide diode lasers (Star Medical Technologies) was used to weld the segments. Five millisecond pulses at 790–810 light was emitted at 2 joules and applied to the tissue with a condenser that created a uniform beam 4×4 mm which was placed on the elastin digest covered by a glass coverslip. Good welds were achieved with up to 10 pulses. A light microscopic photograph of the elastin digest welded to the porcine aorta is shown in FIG. 6.

EXAMPLE 4

Preparation of Elastin-Based Biomaterial and Fusion to Porcine Aorta

Materials:

Bovine nuchal elastin powder (Sigma St. Louis, Mo.) was sifted with a 40 μm screen and swollen with phosphate buffer. Elastin fragments were then reacted with 67 mg of fibrinogen (Sigma) in phosphate buffer, 2 m acid soluble Type 1 collagen (Sigma), 2.8 mg thiourea, 2 mM $Ca^{2+}$, 1 mM $Mg^{2+}$ and 35 units of thrombin and injected into molds and heated to 37° C. One mm thick sheets and tubes of this biomaterial were removed and stored in 33% ethanol for later use.

Figure 5:
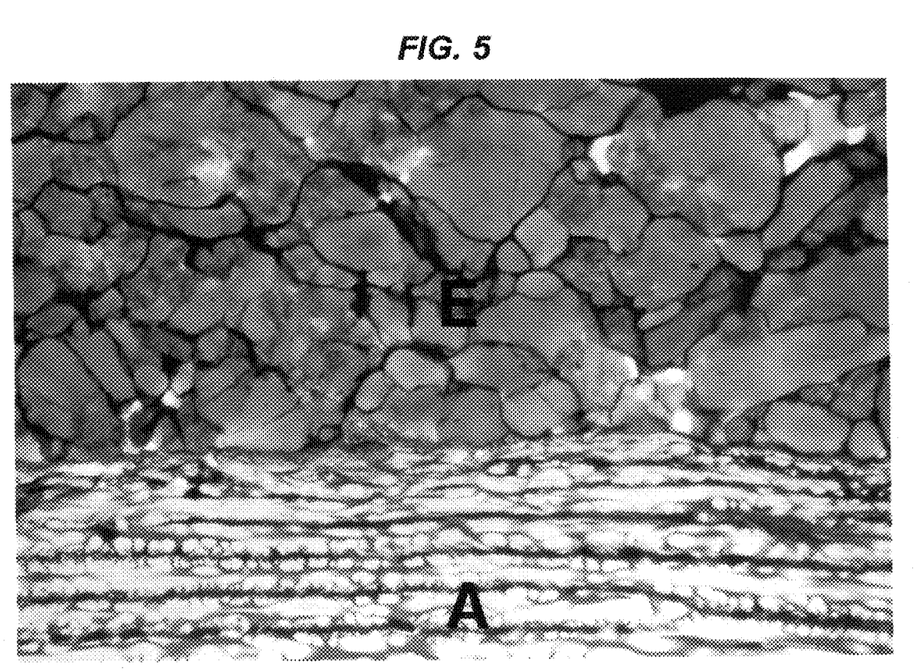
FIG. 5. Light microscopic picture of elastin-based biomaterial fused to porcine aorta using a pulsed diode laser. E=elastin biomaterial; A=aorta.

Indocyanine green dye was dissolved in de-ionized water to provide a 1% solution and applied to the lumenal surface of fresh porcine aorta. The dye was in place for 5 minutes then the residual dye was blotted off. The elastin biomaterial was placed on the ICG stained aorta and covered with a glass coverslip. Laser energy was applied with a condenser which collected the output of an array of gallium arsenide diode lasers emitting light at 800 nm in 5 msec pulses. Six $mm^2$ Spots were irradiated with 2.89 Joules for 1–10 pulses which provided adequate welds. Samples were then bisected and fixed in formalen for microscopic study. FIG. 5 is a light microscopic photograph of such a weld stained with an elastin stain. Excellent welding of the elastin biomaterial to procine aorta is noted with no detetable thermal or other injury to the biomateral or aorta.

All documents cited above are hereby incorporated in their entirety by reference.

One skilled in the art will appreciate from a reading of this disclosure that various changes in form and detail can be made without departing from the true scope of the invention.

What is claimed is:

1. A method for producing an elastin or elastin-based biomaterial fused onto a tissue substrate comprising:

providing a preformed sheet of elastin or elastin-based biomaterial having a first and second outer major surface and a tissue substrate having a first and second outer major surface; and applying an energy absorbing material, which is energy absorptive within a predetermined range of light wavelengths, to one of the first and second outer surfaces of the preformed sheet of elastin or elastin-based biomaterial in an amount which will cause fusing together of one of the first and second outer surfaces of the preformed sheet of elastin or elastin-based biomaterial and one of the first and second outer surfaces of the tissue substrate, the energy absorbing material penetrating into the interstices of the preformed sheet of elastin or elastin-based biomaterial;

irradiating the energy absorbing material with light energy in the predetermined wavelength range with an intensity sufficient to fuse together one of the preformed sheet of first and second outer surfaces of the elastin or elastin-based biomaterial and the tissue substrate; and fusing together one of the first and second outer surfaces of the preformed sheet of elastin or elastin-based biomaterial and the tissue substrate.

2. The method of claim 1, which further includes the step of indirectly irradiating said energy absorbing material by directing the light energy first through the preformed sheet of elastin or elastin-based biomaterial or tissue substrate and then to the energy absorbing material.

3. The method of claim 1, wherein said energy absorbing material comprises a biocompatible chromophore.

4. The method of claim 1, wherein said energy absorbing material comprises an energy absorbing dye.

5. The method of claim 1, which further includes the step of substantially dissipating said energy absorbing material when said preformed sheet of elastin or elastin-based biomaterial and said tissue substrate are fused together.

6. The method of claim 1, which further includes the step of staining the first or second surface of said preformed sheet of elastin or elastin-based biomaterial with said energy absorbing material.

7. The method of claim 1, which further includes the step of applying said energy absorbing material to one of said outer surfaces of said preformed sheet of elastin or elastin-based biomaterial by doping a separate elastin layer with an energy absorbing material, and then fusing the doped separate elastin layer to said preformed sheet of elastin or elastin-based biomaterial.

8. The method of claim 1, wherein the energy absorbing layer is substantially uniformly applied to at least one of said outer surfaces of the said preformed sheet of elastin or elastin-based biomaterial.

9. The method of claim 1, which further includes the step of covering substantially the entire outer surface of said preformed sheet of elastin or elastin-based biomaterial with the energy absorbing material.

10. The method of claim 1, which further includes the step of irradiating the energy absorbing material with light energy at a temperature of from about 40 to 140 degrees C. for period of time which will cause fusing together of one of said first and second outer surfaces of said preformed sheet of elastin or elastin-based biomaterial and one of said first and second outer surfaces of said tissue substrate.

11. The method of claim 1, which further includes the step of irradiating the energy absorbing material with light energy at a temperature of from about 50 to 100 degrees C. for period of time which will cause fusing together of one of said first and second outer surfaces of said preformed sheet of elastin or elastin-based biomaterial and one of said first and second outer surfaces of said tissue substrate.

12. The method of claim 1, wherein the energy absorbing material penetrates into the interstices of said preformed sheet of elastin or elastin based biomaterial an average thickness of from about 0.5 to 300 microns.

13. The method of claim 1, which further includes the step of arranging the magnitude of the wave length, energy level, absorption, and light intensity during irradiation with light energy of the energy absorbing material, and the concentration of the energy absorbing material, so temperature of said first and second outer surfaces of said preformed sheet of elastin or elastin-based biomaterial and the tissue substrate are maintained at from about 40 to 140 degrees C., thereby fusing together said preformed sheet of elastin or elastin-based biomaterial.

14. The method of claim 1, wherein the tissue substrate is a live tissue substrate.

15. A method for using an elastin or elastin-based biomaterial comprising:

providing a preformed sheet of said elastin or elastin-based biomaterial having a first and second outer major surface which is tissue-fusible;

providing a tissue substrate having a first and second outer major surface;

applying an energy absorbing material, which is energy absorptive within a predetermined range of light wavelengths, to one of said first and second outer surfaces of said preformed sheet of elastin or elastin-based biomaterial in an amount which will cause fusing together of one of said first and second outer surfaces of said preformed sheet of elastin or elastin-based biomaterial and one of said first and second outer surfaces of said tissue substrate, said energy absorbing material penetrating into the interstices of said preformed sheet of elastin or elastin-based biomaterial;

irradiating the energy absorbing material with light energy in said predetermined wavelength range with an intensity sufficient to fuse together one of said first and second outer surfaces of said preformed sheet of elastin or elastin-based biomaterial and the tissue substrate; and fusing together one of the first and second outer surfaces of said preformed sheet of elastin or elastin-based biomaterial and the tissue substrate.

16. The method of claim 15, which further includes the step of indirectly irradiating said energy absorbing material by directing the light energy first through said preformed sheet of elastin or elastin-based biomaterial and then to the energy absorbing material.

17. The method of claim 15, wherein said energy absorbing material comprises a biocompatible chromophore.

18. The method of claim 15, wherein said energy absorbing material comprises an energy absorbing dye.

19. The method of claim 15, which further includes the step of substantially dissipating said energy absorbing material when said preformed sheet of elastin or elastin-based biomaterial are fused together.

20. The method of claim 15, which further includes the step of staining the first or second surface of said preformed sheet of elastin or elastin-based biomaterial with said energy absorbing material.

21. The method of claim 15, which further includes the step of applying said energy absorbing material to one of said outer surfaces of said preformed sheet of elastin or elastin-based biomaterial by doping a separate elastin layer with an energy absorbing material, and then fusing the doped separate elastin layer to said preformed sheet of elastin or elastin-based biomaterial.

22. The method of claim 15, wherein the energy absorbing layer is substantially uniformly applied to at least one of said outer surfaces said preformed sheet of elastin or elastin-based biomaterial.

23. The method of claim 15, which further includes the step of covering substantially the entire outer surface of said preformed sheet of elastin or elastin-based biomaterial with the energy absorbing material.

24. The method of claim 15, which further includes the step of irradiating the energy absorbing material with light energy at a temperature of from about 40 to 140 degrees C. for period of time which will cause fusing together of one of said first and second outer surfaces of said preformed sheet of elastin or elastin-based biomaterial and one of said first and second outer surfaces of said tissue substrate.

25. The method of claim 15, which further includes the step of irradiating the energy absorbing material with light energy at a temperature of from about 50 to 100 degrees C. for period of time which will cause fusing together of one of said first and second outer surfaces of said preformed sheet of elastin or elastin-based biomaterial and one of said first and second outer surfaces of said tissue substrate.

26. The method of claim 1, wherein the energy absorbing material penetrates into the interstices of said preformed sheet of elastin or elastin based biomaterial an average thickness of from about 0.5 to 300 microns.

27. The method of claim 15, which further includes the step of arranging the magnitude of the wave length, energy level, absorption, and light intensity during irradiation with light energy of the energy absorbing material, and the concentration of the energy absorbing material, so temperature of said first and second outer surfaces of said preformed sheet of elastin or elastin-based biomaterial and the tissue substrate are maintained at from about 40 to 140 degrees C., thereby fusing together said preformed sheet of elastin or elastin-based biomaterial and the tissue substrate.

28. The method of claim 15, wherein the tissue substrate is a live tissue substrate.

29. A method for producing an elastin or elastin-based biomaterial fused onto a tissue substrate comprising:

providing a preformed sheet of elastin or elastin-based biomaterial having a first and second outer major surface and a tissue substrate having a first and second outer major surface; and applying an energy absorbing material, which is energy absorptive within a predetermined range of light wavelengths, to one of said first and second outer surfaces of said preformed sheet of elastin or elastin-based biomaterial in an amount which will cause fusing together of one of said first and second outer surfaces of the elastin or elastin-based biomaterial and one of said outer surface of said tissue substrate, said energy absorbing material penetrating into the interstices of said preformed sheet of elastin or elastin-based biomaterial;

indirectly irradiating the energy absorbing material by directing the light energy first through said preformed sheet of elastin or elastin-based biomaterial or tissue substrate and then to the energy absorbing material, said light energy being in said predetermined wavelength range with an intensity sufficient to fuse together one of said first and second outer surfaces of said preformed sheet of elastin or elastin-based biomaterial and the outer surface of said tissue substrate; and fusing together one of said first and second outer surfaces of said preformed sheet of elastin or elastin-based biomaterial and the outer surface of said tissue substratel and substantially dissipating said energy absorbing material when said preformed sheet of elastin or elastin-based biomaterial and said tissue substrate are fused together.

30. The method of claim 29, wherein the energy absorbing layer is substantially uniformly applied to at least one of said outer surfaces covering substantially the entire outer surface of said preformed sheet of elastin or elastin-based biomaterial with the energy absorbing material.

31. The method of claim 29, which further includes the step of irradiating the energy absorbing material with light energy at a temperature of from about 40 to 140 degrees C. for period of time which will cause fusing together of one of said first and second outer surfaces of said preformed sheet of elastin or elastin-based biomaterial and one of said first and second outer surfaces of said tissue substrate.

32. The method of claim 29, wherein the energy absorbing material penetrates into the interstices of said preformed sheet of elastin or elastin based biomaterial an average thickness of from about 0.5 to 300 microns.

33. The method of claim 29, wherein the tissue substrate is a live tissue substrate.

* * * * *